US005433716A

United States Patent [19]

Leopardi et al.

[11] Patent Number: 5,433,716

[45] Date of Patent: Jul. 18, 1995

[54] SAFETY CLOSING DEVICE FOR BIOLOGICAL LIQUID CONTAINERS

[75] Inventors: Francesco Leopardi; Sergio Paoletti; Daniele P. Salome, all of Milan, Italy

[73] Assignee: Heisenberg Finance S.A., Luxembourg

[21] Appl. No.: 53,013

[22] Filed: Apr. 27, 1993

[30] Foreign Application Priority Data

May 13, 1992 [IT] Italy .............................. MI92A1139

[51] Int. Cl.[6] .............................................. A61M 5/32

[52] U.S. Cl. .................................... 604/415; 604/403; 604/404

[58] Field of Search ............... 604/110, 111, 192, 244, 604/256, 319, 321, 403–404, 415; 128/912; 206/363–367; 215/247, 249, 251, 252, 204, 208, 217

[56] References Cited

U.S. PATENT DOCUMENTS

| | | | |
|---|---|---|---|
| 2,364,126 | 12/1944 | Cantor et al. | 215/247 |
| 2,487,728 | 11/1949 | Quiring | 215/217 |
| 2,960,247 | 11/1960 | Christie | 215/208 |
| 3,269,576 | 8/1966 | Law | 215/204 |
| 3,734,332 | 5/1973 | Grulich | 215/208 |
| 3,827,593 | 8/1974 | Kramb et al. | 215/208 |
| 3,844,437 | 10/1974 | O'Connor | 215/208 |
| 3,950,917 | 4/1976 | Choksi et al. | 215/204 |
| 4,204,606 | 5/1980 | Micheli . | |
| 4,243,150 | 1/1981 | Gunne et al. . | |
| 4,652,429 | 3/1987 | Konrad . | |
| 4,753,358 | 6/1988 | Virca et al. . | |
| 5,061,263 | 10/1991 | Yamazaki et al. . | |

FOREIGN PATENT DOCUMENTS

| | | | |
|---|---|---|---|
| 770450 | 10/1967 | Canada | 215/208 |
| 0391461 | 10/1990 | European Pat. Off. . | |
| 0454493 | 10/1991 | European Pat. Off. . | |
| 2820207 | 12/1978 | Germany | 215/247 |
| 1294165 | 10/1972 | United Kingdom | 215/208 |
| 2034289 | 6/1980 | United Kingdom | 215/208 |
| 2228730 | 9/1990 | United Kingdom . | |
| 9006267 | 6/1990 | WIPO . | |

*Primary Examiner*—Randall L. Green
*Assistant Examiner*—P. Zuttarelli
*Attorney, Agent, or Firm*—Ostrolenk, Faber, Gerb & Soffen

[57] ABSTRACT

A safety closing device for containers of biological liquids and, particularly, for test tubes used for the drawing, transport and/or analysis of blood. The safety closing device includes an undercap and a cap, both with central portions made of a perforable material. The central portion of the undercap is sealingly locked on the edge of the test tube and the central portion of the cap is sealingly locked on the side facing the undercap. A locking mechanism, that can only be intentionally disengaged, mechanically couples the cap to the undercap, and secures the cap/undercap assembly onto the prearranged open end of the test tube.

44 Claims, 8 Drawing Sheets

SAFETY CLOSING DEVICE FOR BIOLOGICAL LIQUID CONTAINERS

BACKGROUND OF THE INVENTION

1. Field of the Invention

The present invention relates to safety closing devices for containers of biological liquids, particularly for test tubes holding blood. The closing devices are comprised of substantially two components: (1) an undercap mounted on the open end of the container, having a bottom of perforable material for allowing the insertion of a drilled rod-shaped element into the container; and (2) a cap, also made of perforable material, mounted on the undercap for assuring the sealed closing thereof.

2. Description of the Prior Art

Closing safety devices comprising a cap and an undercap for the closing of test tubes under vacuum, are known. The purpose of the cap/undercap assembly is to assure both the sealing of the vacuum present in the inside of the container prior to filling and the sealing of liquid that afterwards is introduced therein. To introduce the liquid into the test tube under vacuum, a support device on which is mounted a needle with a double point, the so-called "needle holder", is usually used. One point of the needle is inserted into the part of patient from which it is necessary to extract the liquid, for example, blood, while the other point is inserted through the perforable cap and undercap and extends into the inside of the test tube. Collection of liquid within the test tube by vacuum occurs in this manner without removing the cap and undercap from the test tube. After the suction operation is completed, the test tube is extracted from the needle holder and the needle is extracted from the human body and then removed from the needle holder and disposed of, being of no more use while the above mentioned needle holder can be used for another drawing of liquid from the human body.

The test tube holding the drawn blood sample can then be sent to the laboratory perfectly sealed. During analysis, the cap is usually removed from the undercap to allow the extraction of the liquid from the test tube, using a proper drawing device, such as a pipetting, a tip for a pipette device, or a needle, which perforates and passes through the undercap to enter the inside of the test tube. In particular, if the undercap includes one or many through incisions or slits with flexible edges in its bottom, as described in the European Patent No. 0391461 filed on Mar. 26, 1990, the drawing device crosses through the slits between the flexible edges and, after the removal of the device from the test tube, the edges close together to prevent undesirable leakage of liquid remaining in the test tube. As disclosed in the above-mentioned Italian Patent, the undercap, having the shape of a glass, is pressure-fitted into the opening of the test tube. Similarly, the cap is pressure-fitted into the inside of the undercap. So, the sealing between the undercap and test tube and between the undercap and cap is assured by radial pressure.

Closing devices of this type do not offer sufficient guarantees for a safe closing, because the undercap, coupled with the internal surface of the test tube by only radial pressure, can be accidentally removed from the test tube causing the blood to spill, with a consequent risk of infection to the operator in charge of the drawing operation or handling the test tube. In practice, the undercap can be accidentally disengaged from the test tube by the dragging caused by the cap during its removal, indeed, ageing of the contacting materials of the cap and undercap can produce so strong a coupling that the two components behave as if they are a single piece. Furthermore, the undercap can be accidentally removed from the test tube when the pipette or the tip, used for the drawing of the blood sample, is removed from the test tube.

On the other hand, if it is necessary to remove the undercap from the test tube for the purpose of completely opening the mouth of the tube, difficulty may arise when trying to extract the undercap from the test tube, due to the high adhesion that can occur between the undercap and test tube. The increased effort needed to extract the undercap and the sudden release of the undercap from the test tube can cause a spray of blood outward, exposing the operator at risk of contamination through the effect of vaporization and/or aerosol formation of the blood.

Naturally, even when the test tube is filled at normal room pressure and then closed again by the known closing devices, removal of the undercap can occur for example, during its transport due to accidental contacts or expansion of internal gases. In any case, when the undercap is removed, it can be contaminated with blood and therefore represents a high risk, both for resting the undercap in any place without causing pollution to the environment and for handling the undercap for repositioning the same on the container, if it is necessary to close the container again.

Further, the re-closing by the known closing devices requires the insertion of the cap into the undercap. This operation is difficult due to the air present in the cavity of the undercap, which hinders cap insertion.

Finally, the above-mentioned closing devices have an undercap which extends inside the container, reducing the utilizable volume of the container.

SUMMARY OF THE INVENTION

An object of the present invention is to provide a closing device for containers of biological liquids of the type described above, that allows a hermetic and more reliable replaceable closing of the container and, above all, prevents accidental separation of the cap from the undercap, and the undercap from the container, and at the same time, allows the opening of the container only by an intentional removal of both the undercap and cap, thereby completely avoiding situations where the operator in charge of the filling, transport, drawing and analysis, etc. of the liquid is under risk of infection. A further object of the invention is to provide a safety closing device that prevents the operator from coming into contact with the blood during and after the partial or total removal of the caps.

Another important object of the invention is to provide a safety closing device also utilizable for the closing of test tubes holding blood of which the erythrosedimentation rate (E.S.R.) is to be measured.

Another object is to obtain a safety closing device that allows the utilization of the entire internal volume of the container.

The above mentioned objects are fulfilled by the present invention, which comprises a safety closing device in which the undercap and cap each include at least a central elastic perforable portion formed by one or many parts. The portions of the undercap and cap are sealingly locked by the front side on the edge of the container and on the side facing the undercap, respectively, by axial pressure which is applied and/or kept by locking means only intentionally disengageable by an operator. The locking means allows simultaneously reciprocal mechanical coupling of the portions and of the assembly thereof onto the prearranged container open end.

To provide the locking means, the undercap and cap, according to a preferred embodiment, each include, in addition to the central portion, a partially threaded axial external cylindrical portion. The threaded part of the external portion of the undercap is engaged on one side with the corresponding threaded part of the threaded external portion of the cap, and on the other side with a corresponding threaded part of the container external wall.

The two portions of both the cap and undercap can be made as either a single piece or as two parts of different material closely joined with one another. In the latter case, the materials selected should be the more suitable in relation to the particular sealing or mechanical anchoring function that each portion performs. The central portions of the cap and undercap can be made of a soft plastic material, the external portions made of a hard plastic material, and the connection of the two portions can be made by a co-molding or overmolding process. The reliability of the double axial seal and the particular connection system of the parts that form the closing system guarantee absolute hermetic sealing of the container and furthermore prevents any undesirable opening caused by accidental separation of the cap and undercap. Therefore, access to the inside of the container is only possible by rotating the cap and undercap and clearly by perforating the cap/undercap assembly with a needle.

For even better protection against accidental opening of the container, the thread provided between the coupled external portions of the cap and undercap, and the thread provided between the external portion of the undercap and the external portion of the container, have opposite winding directions, so that special attention of the operator is required when completely opening them. In accordance with the invention, in order to prevent presence of blood in the area of the central portions of the cap and undercap subject to the needle's passage, these portions adhere perfectly with one another and no free space exists therebetween for receiving blood during the insertion of the needle into the container. Therefore, any risk of infection to the operator contacting blood which could be present between the central portions when the cap is removed is avoided.

According to another feature of the invention, in order to enable the removal of the undercap from the container, and then to close it again without any risk of infection, the external cylindrical portion of the undercap surrounding the container extends axially downward from the central portion, the bottom of which can be contamined with blood along a suitable length to make it practically impossible for the operator to come in contact with the contaminated central portion, when the undercap is removed.

According to a further embodiment of the invention, to allow the introduction of a drilled rod-type element into the container for the purpose of analysis or data survey of the blood, the undercap includes a through incision in its bottom. The incision is made by one or more flexible edges or by a central pre-established fracture area obtained by means of a reduced thickness and/or tearing or preincision lines. The flexible edges of the incision or the flexible edges formed after the perforation of the area with preestablished fracture become perfectly sealed after the withdrawal of the drilled rod-type element from the test tube.

According to another embodiment of the invention, the area with the preestablished fracture can be made by means of a circular tearing or preincision line extending almost 360 degrees on the bottom of the undercap. In this case, the rod-type element that perforates the area which can have a reduced thickness, is, for instance, formed by a graduated pipette suitable for measuring the blood erythrosedimentation rate (E.S.R.).

Furthermore, the axial sealing assured by the safety closing device of the invention engages only the well-defined crown of the undercap. Therefore, the internal surface of the undercap can be flat and coplanar with the container edge, thereby achieving the advantage of a greater utilizable internal volume of the container.

Further characteristics and advantages of the invention will be evident from the following description of some embodiments of the invention made with reference to the accompanying drawings.

DETAILED DESCRIPTION OF THE PREFERRED EMBODIMENTS

Figure 1:
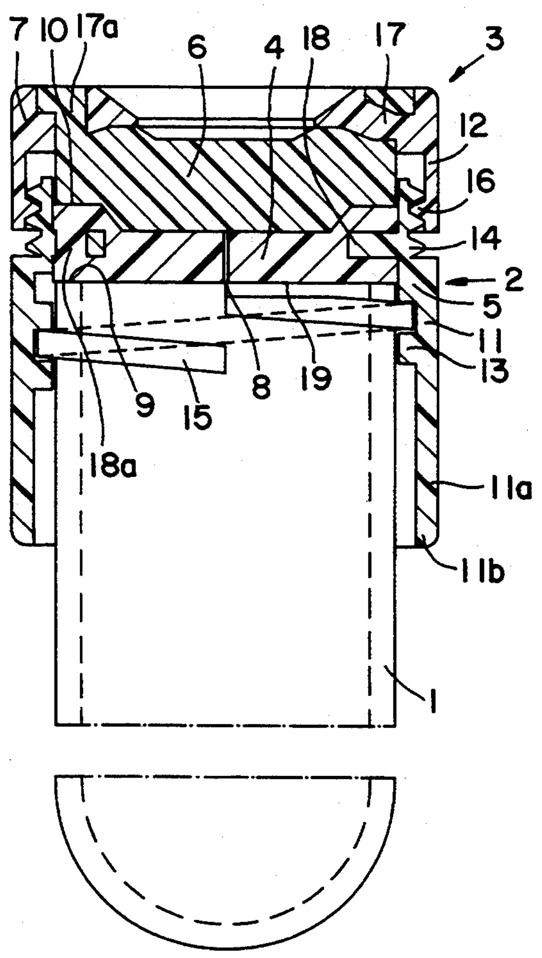
FIG. 1 illustrates a side view of the biological liquid container and a cross-sectional view of the safety closing device according to the first embodiment of the invention.
Figure 2:
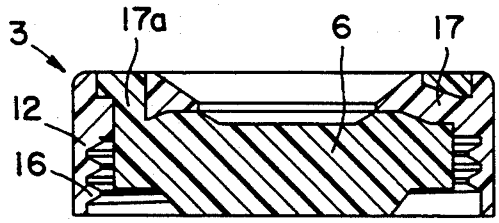
FIG. 2 shows a cross-sectional view of the cap of the closing device of FIG. 1.
Figure 3:
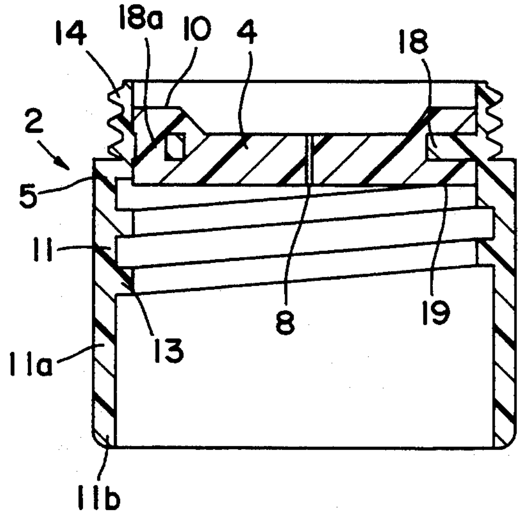
FIG. 3 is a cross-sectional view of the undercap of the closing device of FIG. 1.

Referring first to FIGS. 1, 2, and 3, the safety closing device of the present invention includes a cylindrical container 1 capable of containing a biological liquid, such as the test tube referred to herein, undercap 2 and cap 3, either assembled on the test tube or separated. Undercap 2 includes a central portion 4 and an external portion 5 closely joined to form a single piece. Similarly, the cap 3 includes a central portion 6 and an external portion 7, also closely joined to form a single piece.

The central portion 4 of undercap 2 has an incision 8 formed by two flexible edges that, in normal handling conditions of the test tube, fit perfectly together to avoid accidental leakage of the contained liquid. Many methods can be used to produce incision 8, for example, by a cutting operation or the direct formation of the incision during the molding phase of the central portion. The execution of the incision can occur in a plane coinciding with or parallel to, or sloped with respect to the axis of the undercap. A coinciding or parallel incision obtained by cutting is preferred because the corresponding profile of flexible edges helps to seal the liquid held in the test tube.

The internal central portions 4 and 6 perform the function of assuring the hermetic closing of the container and therefore are made of a suitable soft plastic material and are axially tightened against the edge 9 of the test tube and the facing edge 10 of the undercap, respectively.

In contrast, the external portions 5 and 7 perform the function of assuring a mechanical coupling of the parts, by an axial tightening pressure, and therefore are formed by a suitable hard and strong plastic material. As shown in detail in FIGS. 2 and 3, portion 5 includes a cylindrical axial wall 11 which is connected with the central portion 4 of the undercap and extends partially around the test tube 1 and the central portion 6. Portion 7 includes a cylindrical axial wall 12 which is connected with the central portion 6 of the cap. Walls 11 and 12 are provided with threads 14 and 16, having single or multiple starts, for their reciprocal engagement. Wall 11 also includes a thread 13 which engages with a thread 15 of the external wall of the test tube. Thread 14 is external to the wall 11, while thread 16 is internal to the wall 12. However, threads 14 and 16 could be formed in the inside and in the outside of the related walls, respectively.

To achieve the hermetic closing of the container, the material forming the central portions 4 and 6 can be made of a rubber, preferably a bromine-buthylic, or a thermoplastic elastomer. In any case, a soft material for adhesion to the edges 9 and 10 of the test tube and of the undercap when the cap and undercap are completely screwed together, is preferred. The material must also be perforable to permit easy access through it by, for example, a hypodermic needle, during the drawing of the liquid in the test tube.

The external portions 5 and 7 can be made of a thermoplastic resin or of another material harder than the material forming the central portions, in order to withstand the operations of screwing and unscrewing and above all, the final tightening operations of the cap and undercap. It is especially advantageous for the central portions 4 and 6 to be made of an injection moldable material, so that a co-molding or overmolding process to form the close connection with the external portions 5 and 7 can be used. In order to guarantee a perfect anchoring and connection of these portions, the portions should include complementary engaging elements, such as protrusions and/or corresponding axial holes, that are reciprocally co-penetrated during the molding phase. In this manner, the two portions form one unit, separable only by breakage. Furthermore, the materials of reciprocal co-penetrating parts also reinforce the annular area of junction of the central and external portions to obtain an effective transmission of the axial thrust on the edges 9 and 10 after screwing the undercap 2 and cap 3, and in conclusion, to guarantee a perfect sealing on the edges.

In FIGS. 1, 2, and 3, the materials of reciprocal co-penetrating parts are designated by reference numerals 17, 17A, 18 and 18A. However, it is obvious that different types of reciprocal joints can be used to make the close connection of the parts during the co-molding phase. The above-mentioned closing device guarantees a perfect closure of the test tube so as to maintain the vacuum made inside before it was closed, or to assure perfect containment of the liquid sucked or otherwise introduced into the tube.

Further, the device allows the complete use of the volume of the test tube, as the bottom central portion 4 of the undercap 2 does not extend into or engage any internal space of the container.

To increase closing safety, the threads 14 and 16 between the undercap 2 and cap 3, and the threads 13 and 15 between the undercap 2 and test tube 1, have opposite winding directions. Preferably, the thread between the cap and undercap is of a common clockwise type, because the unscrewing of the cap 3 only does not involve dangerous conditions, while the thread between the undercap and the test tube is of an unusual counterclockwise type, because removal of the undercap involves potential dangerous conditions. This manner of closure has a double advantage: on the one hand, it is avoids the accidental unscrewing of both parts when it is desired to remove one only, and on the other hand, it forcibly calls the operator's attention to the removal process. A further safety factor can be introduced by providing a force condition which must be exceeded in order to initiate the unscrewing of the undercap from the test tube.

Further, due to the presence of the thread, the action of removing the undercap from the test tube does not involve a violent removal, and therefore the risk of blood spraying out of the tube to contaminate the operator with blood vaporization or aerosol formation is eliminated.

Due to the threads being used as axial tightening means, and also due to the opposite screwing direction and the force which must be exceeded, it is guaranteed that an accidental opening of the test tube will definitely not occur. Therefore, in the closing device according to the present invention, the risk of accidental discharge of contaminated blood or other biological liquid does not exist. As previously mentioned, it is absolutely required that the operator pay special attention during the opening of the test tube; i.e., in accordance with the present invention, the operator must intentionally make determinate specific separate rotations of the cap and undercap.

In order to avoid leakage of liquid between the facing surfaces of the central portions 4 and 6 at the moment in which the needle crosses the portions during introduction of blood into the under vacuum, these surfaces, subject to the needles passage are suitably shaped to adhere perfectly with one another. In this manner, no free space in the intermediate zone is formed in which space the blood could be sucked during the passage of the hypodermic needle exposing the operator to risk of infection after removal of the cap 3. For example, the coupled surfaces could assume a concave/convex form with contact surfaces in a curved or plane shape. The surface of the undercap should preferably be made in concave form and, and accordingly, the surface of the cap is made in convex form as shown in FIGS. 1, 2, 3. The cap and undercap are shaped to guarantee an effective sealing of the edges 9 and 10 of the central portions, respectively.

During the drawing of blood from a patient using a double point hypodermic needle, one point is inserted into the blood vessel of the patient and the other point extends through the portions 4 and 6 and into the inside of the test tube already under vacuum. Under the effect of this vacuum, the blood is sucked into the test tube without the necessity for removing the cap 3 and undercap 2. Then the needle is extracted from portions 4 and 6 and the blood remains inside the test tube with no possibility of leakage. Even when the cap 3 is removed, leakage of blood through the incision 8 is not possible as its flexible edges close perfectly after the removal of the hypodermic needle.

To make the necessary blood tests, the test tube can remain closed, and a simple device suitable for perforating the cap and undercap can be used, or the cap 3 can be removed. In this case, the device for perforating and withdrawing the desired amount of liquid can be a pipette, a pipette tip or any other device. The selected drawing device is inserted through the flexible edges of the incision 8 which separate to allow passage of the device therethrough. Once this operation is completed, the device is removed and, if desired, the cap can be easily and safely screwed onto the undercap restoring the same initial condition of hermetic closing of the test tube. Upon extracting the device from the incision 8, the flexible edges reclose perfectly so that even without screwing the cap back on the undercap, the blood cannot leak from the test tube. Therefore, any risk of contamination during drawing, analysis and/or transport of blood is eliminated.

A further safety feature for preventing contact with the blood present in the test tube includes the elongation of the cylindrical wall 11 of the undercap by wall or shirt 11*a* which surrounds the test tube and extends downward a certain length over the engagement zone with the same test tube so that its end 11*b* is sufficiently spaced from the internal surface 19 of the central portion 4 of the undercap 2. The extension of the wall 11*a* is related to the internal diameter of the test tube. If this diameter increases, the length of the extension increases. Therefore, when the undercap, for any reason, must be removed from the test tube, the chance of contact with the internal surface 19 of the undercap is highly reduced, thereby avoiding operators contact with blood contaminated parts.

FIGS. 4 to 27 illustrate different embodiments related to the form and number of pieces forming the cap and undercap, and other embodiments of the axial tightening and coupling means of the components forming the closing device, and further possible applications of the device. Identical parts have been indicated with the same identical reference symbols as those in FIGS. 1–3, while corresponding parts are indicated with the same reference symbols, followed by a capital letter.

Figure 4:
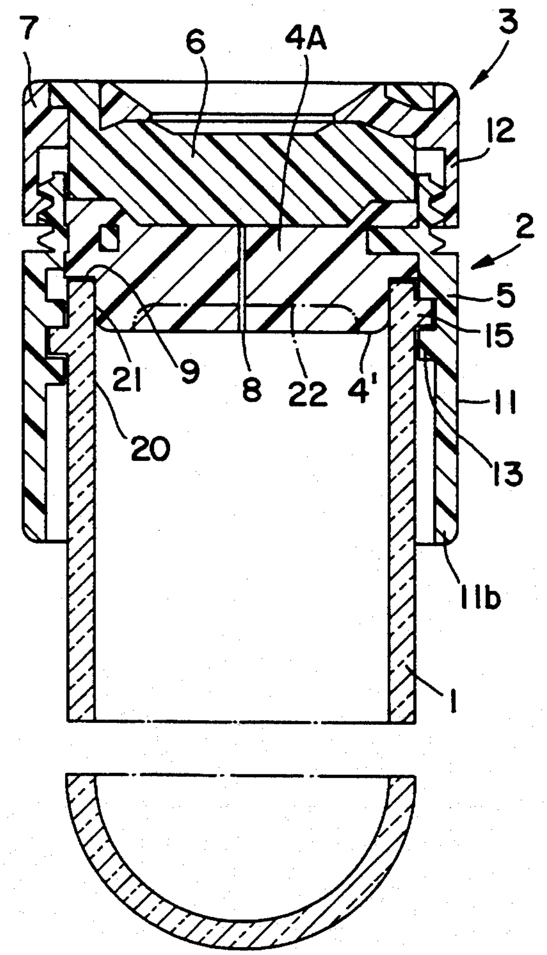
FIG. 4 shows a cross-sectional view of the container and safety closing device according to a second embodiment of the invention.

The device shown in FIG. 4 is identical to the device of FIG. 1, with the difference that the central portion 4A of the undercap 4A has a central axial extension 4' that is press-fitted into the opening 20 of the test tube 1. The lateral contact zone between extension 4' and opening 20 is indicated by numeral 21. Thus, the tightness is increased because a radial sealing on the zone 21 is added to the axial sealing on the edge 9. As indicated by the dotted lines, the axial extension 4' can have a central hollow or cavity 22 at its end, to increase the internal available volume of the test tube.

Figure 5:
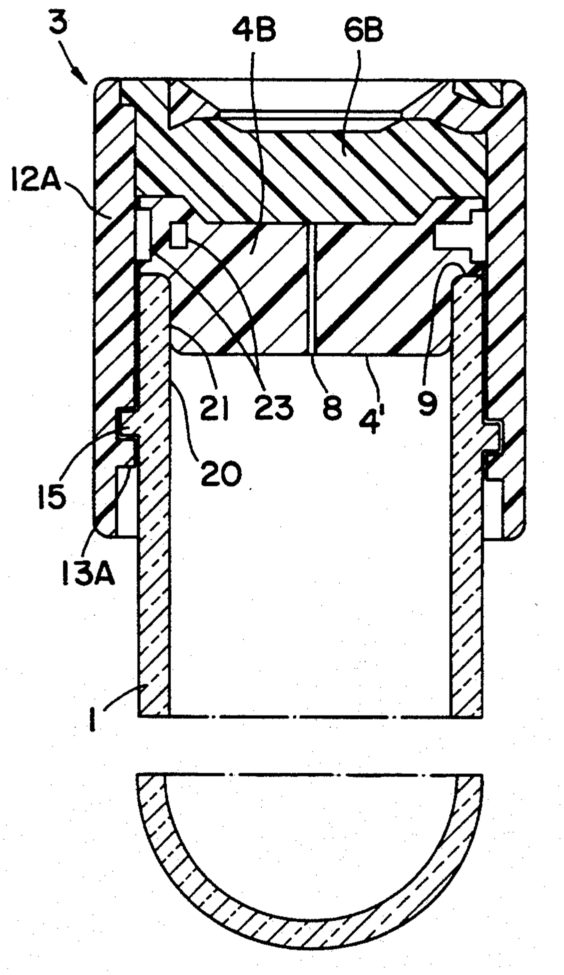
FIG. 5 shows a cross-sectional view of a third embodiment of the closing device of the invention.

The closing device of FIG. 5 includes a cap 3 having an external portion formed by an elongated wall 12A which sealingly locks portions 4B and 6B together and against the test tube 1. Indeed, wall 12A is engaged by the thread 13A with the thread 15 of the test tube compressing the central portion 6B of the cap 3 against the central portion 4B of the undercap 2 and this last portion against the edge 9 of the test tube. Like the embodiment of FIG. 4, the central portion 4B includes an axial extension 4' pressed into the open end 20 of the test tube.

In a manner similar to FIG. 1, the central portion 6B is joined with the external portion 12A of the cap by a co-molding or overmolding process, while the central portion 4B of the undercap can form a separate molded piece. When a particularly elastic material is selected for portion 4B, in order to improve its handling and stiffening a ring 23 made of a more rigid material can be incorporated therein.

Figure 6:
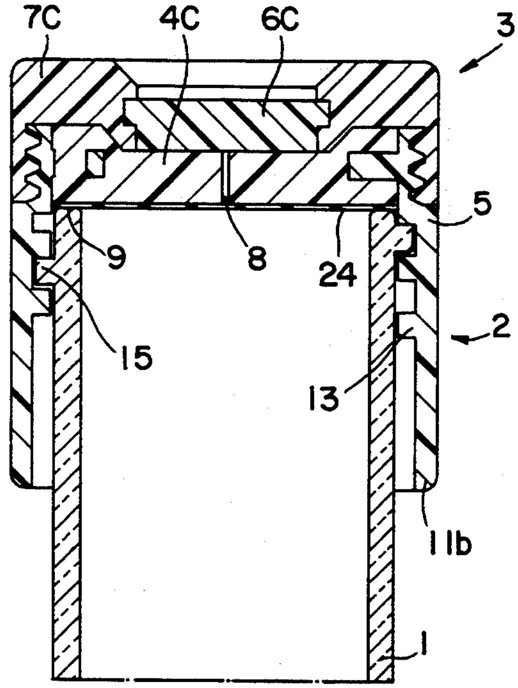
FIG. 6 shows a cross-sectional view of a fourth embodiment of the closing device of the invention.

The device shown in FIG. 6 has a central portion 4C and external portion 5 of the undercap 2 joined with one another by a co-molding or overmolding process, as in the case of FIG. 1, while the central portion 6C of the cap 3 forms a separate piece obtained by molding and is inserted into the related external portion 7C. As shown in the drawing, portions 6C and 7C of the cap have suitable joining shapes, wherein one portion 7C can receive and elastically retain the other portion 6C, providing a tight mechanical connection. Further, a perforable sheet 24, of any impermeable material that assures vacuum sealing, such as a polyethylene-lined aluminum sheet or non-polyethylene-lined aluminum sheet, is fixed, for example by glue, to the edge 9 between portion 4C and the test tube to assure a better vacuum inside the test tube until the sheet is perforated by a needle or a similar device for introducing blood into the test tube.

Figure 7:
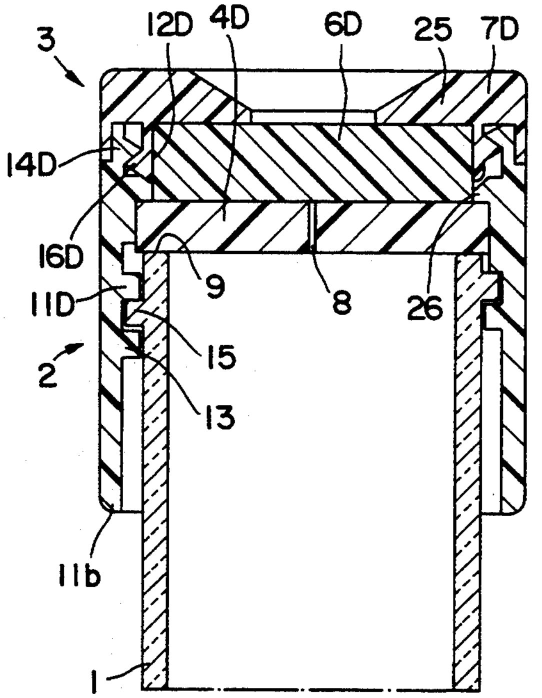
FIG. 7 is a cross-sectional view of a fifth embodiment of the closing device of the invention.

The closing device of FIG. 7 includes central portions 4D and 6D, formed by two perforable elements having a cylindrical shape. These elements can be obtained by molding or sheared from a sheet and then assembled during the assembly of the closing device. Locking of these elements with the test tube is obtained by the engagement of threads 13 and 15 and threads 14D and 16D which causes, by means of the internal annular edges 25 and 26 of the cap and undercap, respectively, the tightening of the portions 6D and 4D against the edge of the test tube during the screwing movement of the external walls 11D and 12D. Wall 11D is coupled to the external wall of the test tube and to external wall 12D of the cap by threads, as in the case of FIG. 1, with the difference that thread 14D is internal to wall 11D and thread 16D is external to the wall 12D.

Figure 8:
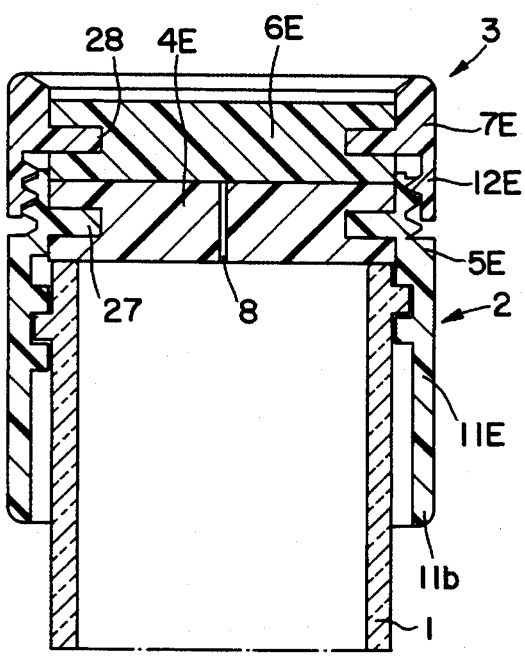
FIG. 8 is a cross-sectional view of a sixth embodiment of the closing device of the invention.

The device of FIG. 8 includes identical cylinders 4E and 6E forming the central portions of the undercap 2 and cap 3. Because these cylinders are the same, used twice, there is a manufacturing advantage as they are produced separately and then elastically encased in the related internal annular edges 27 and 28 of the external portions 5E and 7E of the undercap and cap, respectively.

Figure 9:
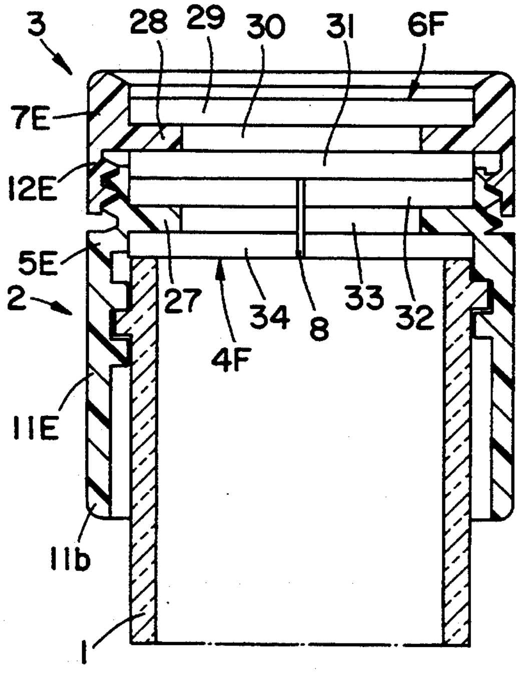
FIG. 9 is a cross-sectional view of a seventh embodiment of the closing device of the invention.

FIG. 9 shows the central portions of the cap and undercap, each formed of three pieces. The central portion 6F of the cap 3 is formed of three disks made of a perforable material obtained by molding or shearing and fixed afterwards, e.g. by glue, to one another and to the annular internal edge 28 of the external wall 7E. An external disk 29 can be affixed onto the edge 28 and then the intermediate disk 30, having a smaller diameter, can be affixed to the inside of the edge 28. Finally, the other external disk 31 can be affixed onto the other side of the edge 28 and on the intermediate disk 30. Similarly, the central portion 4F of the undercap 2 which again includes incision 8, is formed by three disks 32, 33 and 34 fixed by the above mentioned method to the internal edge 27 of the wall 5E of the undercap.

Figure 10:
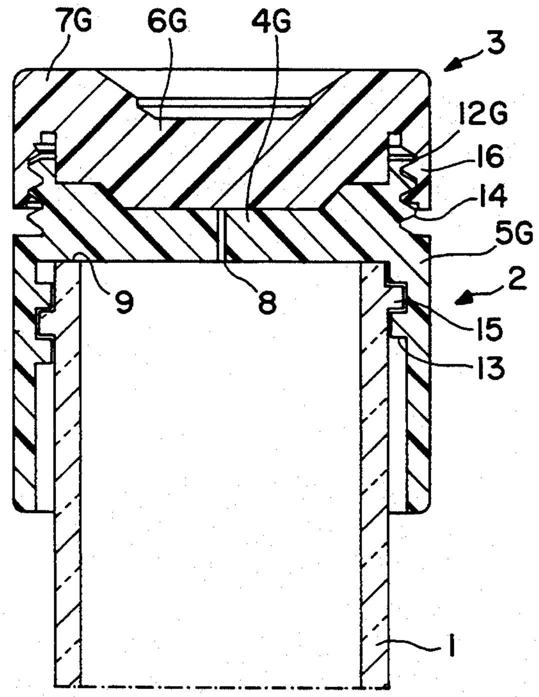
FIG. 10 shows, in cross-sectional view, another embodiment of the safety closing device of the invention.
Figure 11:
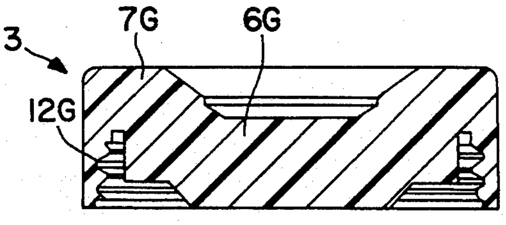
FIG. 11 illustrates a cross-section of the cap of FIG. 10.
Figure 12:
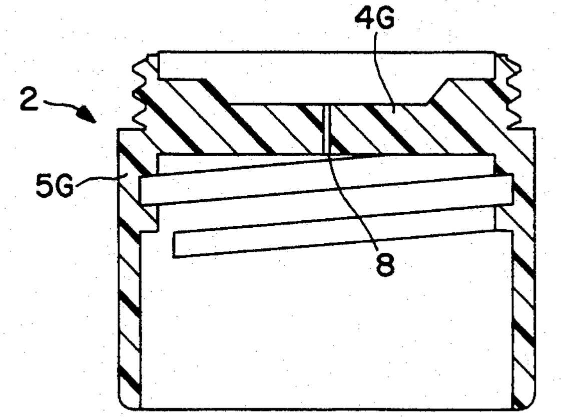
FIG. 12 illustrates a cross-section of the undercap of the closing device of FIG. 10.
Figure 13:
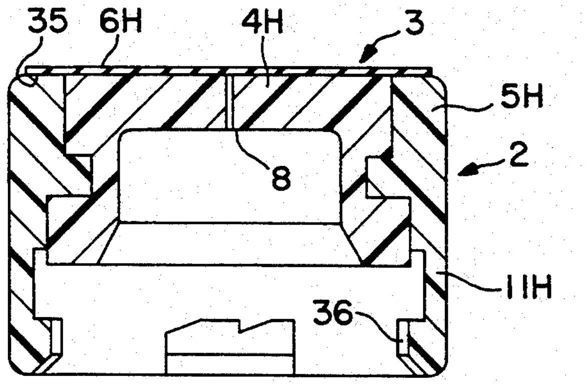
FIG. 13 illustrates a cross-section of a cap and undercap assembly according to a ninth embodiment of the invention.
Figure 15:
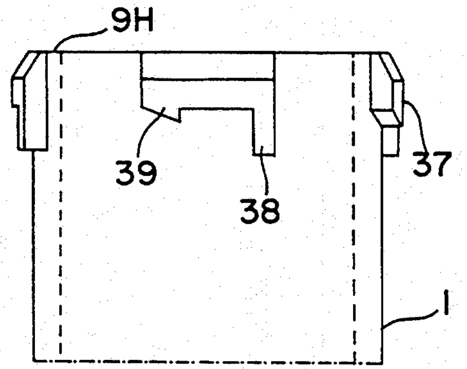
FIG. 15 is a side view of the container before it is coupled with the cap-undercap assembly of FIG. 13.
Figure 14:
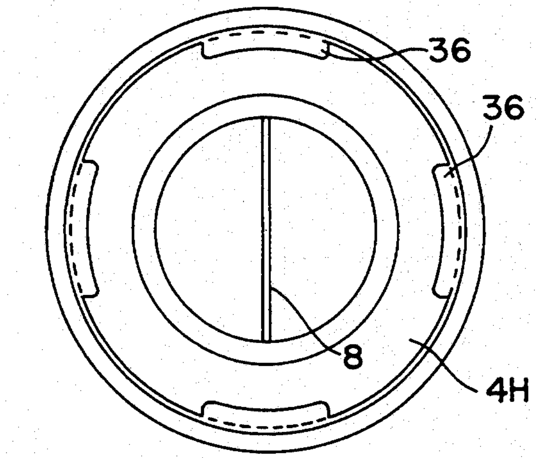
FIG. 14 is a bottom view of the cap-undercap assembly of FIG. 13.
Figure 16:
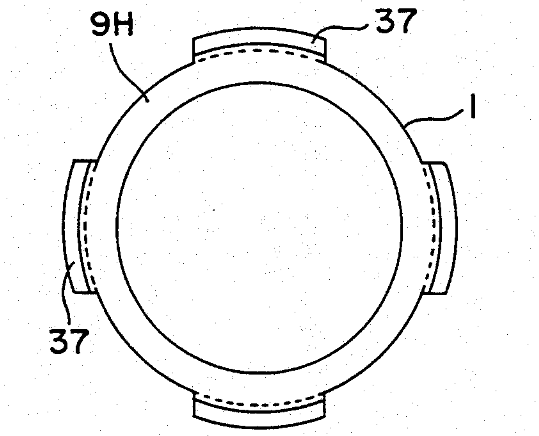
FIG. 16 is a plan view of the container of FIG. 15.

The closing device of FIG. 10 is essentially similar to the device of FIG. 1, but with the difference that the central and external portions 4G and 5G of the undercap 2 form a single unitary piece and the central and external portions 6G and 7G of the cap 3 are also formed of a single unitary piece. FIGS. 11 and 12 show the cap and undercap before assembly. In this embodiment, the material of the cap and undercap have characteristics suitable for assuring the flexibility and the perforability necessary for achieving perfect sealing and allowing the passage of a hypodermic needle therethrough, as well as being sufficiently strong to resist the screwing and unscrewing of the cap and undercap. A sole thermoplastic resin such as polytetrafluoroethylene, polyethylene having a high or low density, polyethylene acetal resin, vulcanizable rubbers or thermoplastic elastomers of suitable hardness, etc., can be used.

It should be clear that only the undercap including both portions or only the cap including both portions could form an integral piece. The devices described so far, disclose that the locking of the cap-undercap assembly to the test tube is obtained by rotational movement.

Another embodiment of the invention that also requires a rotational locking is shown in FIGS. 13 to 17. With reference to FIG. 13, the undercap 2 is again made by a joint between the internal portion 4H and the external portion 5H, while the cap 3 is simply made of a sheet of impermeable perforable material 6H which is fixed for example by glue, to the edge 35 of the external portion 5H. The joint between the portions 4H, 7H is made similar to that shown in FIG. 8, but it is clear that any other kind of joint is possible.

Figure 17:
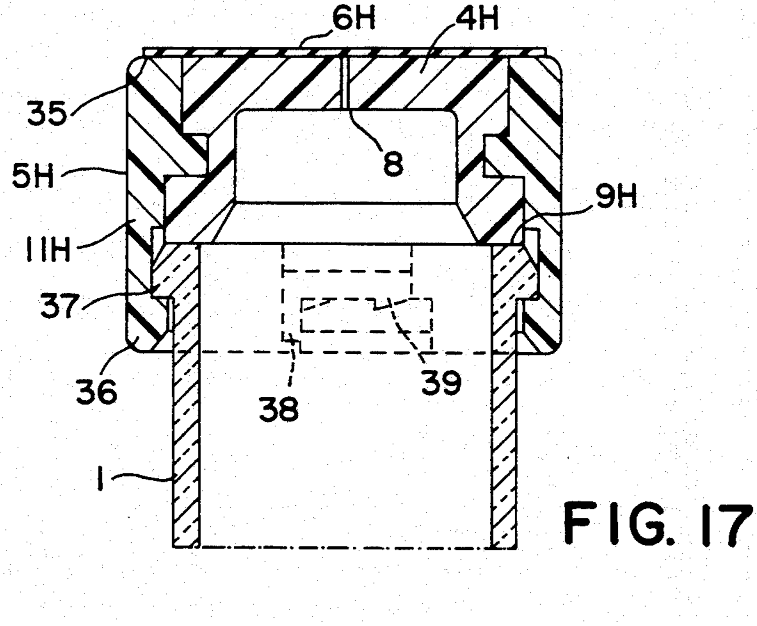
FIG. 17 shows the cap-undercap assembly of FIG. 13 mounted on the container of FIG. 15.

To couple the cap-undercap assembly to the test tube 1, the wall 11H includes at its end some internal radial projections 36 having the form of circular sectors. As shown in FIG. 17, the projections 36 engage with corresponding external radial projections 37, also made in the form of circular sectors, of the test tube 1.

To close the test tube 1, the cap-undercap assembly is axially forced downward with the undercaps central elastic portion 4H, against the edge 9H of the test tube until the radial sectors 36 of the undercap overcome the spaces between the radial sectors 37 of the test tube. Then, the cap-undercap assembly is rotated until sectors 36, 37 are engaged. So, the coupling of the parts is produced by an insertion joint connected by the so-called bayonet system, and not by threads as in the preceding embodiments of the invention. Suitable rotation stop devices 38 and also anti-unscrewing devices 39, having the desired disengaging force, can be provided on the external wall of the test tube and on the surmounting internal part of the undercap. The sheet of impermeable material 6H seals the closing device until the moment it is torn. Sealing is achieved by pressure applied between the external portion 5H and the internal elastic portion 4H and between this elastic portion and the edge 9H of the test tube, and by the sheet 6H locked on the front side of the upper circular edge 35 of the undercap.

Figure 18:
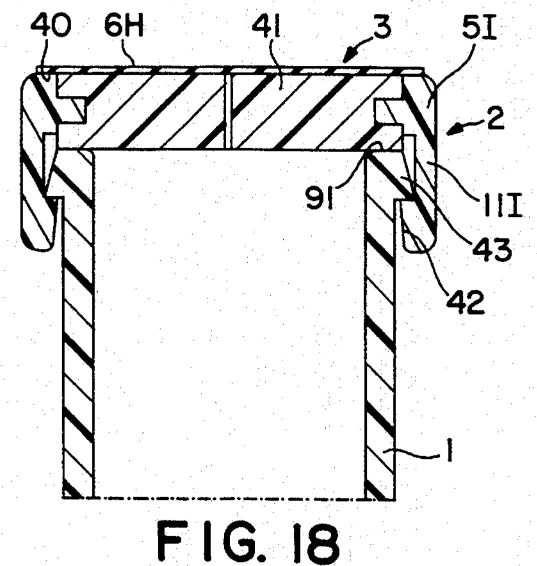
FIG. 18 shows, in cross-section, another embodiment of the safety closing device and container of the invention.
Figure 19:
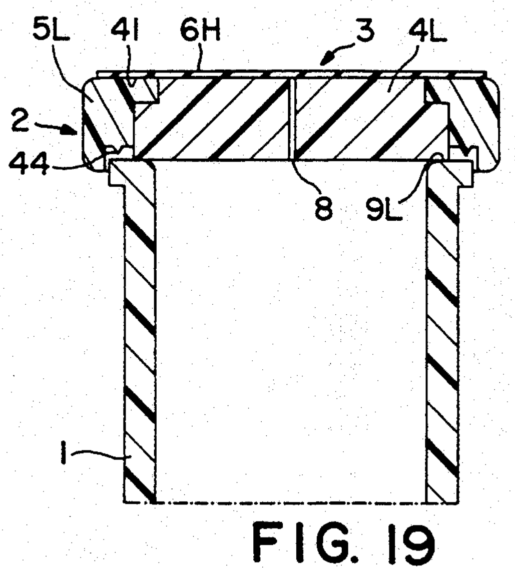
FIG. 19 is a cross-sectional view of a tenth embodiment of the safety closing device and container.
Figure 20:
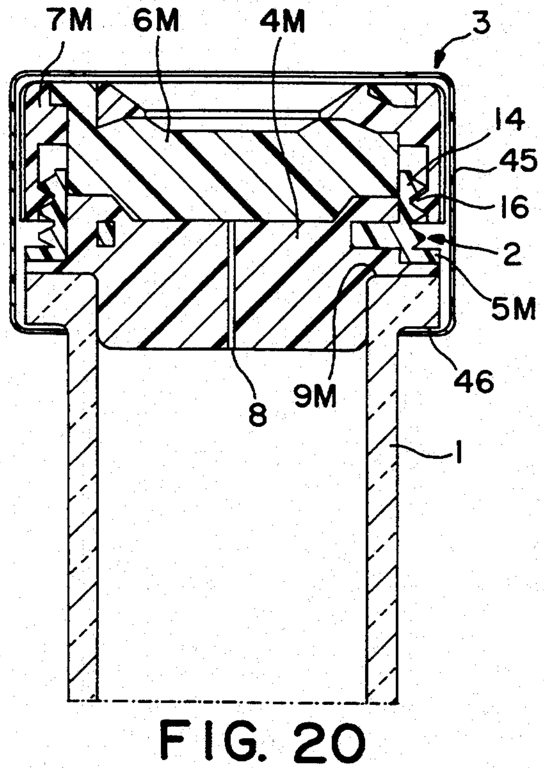
FIG. 20 illustrates in cross-section a further embodiment of the safety closing device and container.

In the embodiments shown in FIGS. 18, 19 and 20, the coupling of the cap-undercap assembly to the test tube is obtained simply by an axial tightening action. In particular, the devices of FIGS. 18 and 19 include a cap again made of a sheet of an impermeable material 6H sealingly fixed to the edges 40 and 41 of the external portions 5I and 5L of the undercap 2, respectively. The coupling of the cap-undercap assembly shown in FIG. 18 is formed by a joint between an internal circular edge 42 on an end of the wall 11I and a corresponding external circular edge 43 of the test tube. The locking of the closing device occurs when the cap-undercap assembly is forced onto the end of the test tube until the edge 42 of the undercap passes over and engages the corresponding edge 43 of the test tube, while the central portion 4I of the undercap is simultaneously compressed against the edge 9I of the test tube.

FIG. 19 shows the connection of the cap-undercap assembly onto the test tube again obtained by compression, in particular the central portion 4L is compressed against the edge 9L of the test tube. The irreversible coupling is obtained by fusion welding, e.g. by ultrasonic welding of an annular element 44, preferably having a triangular profile, shown on the face of the portion 5L extending toward the edge of the test tube. Element 44, for clarity's sake, is shown in FIG. 19 spaced from the edge 9L in an inoperative condition. As an alternative, element 44 can be placed on the edge 9L of the test tube facing a plane surface of the portion 5L. The element 44, fused to make a single piece between the undercap and test tube, is known as an "ultrasonic wave-guide".

FIG. 20 discloses a device with a locking mechanism which is activated by axial tightening of the cap-undercap assembly against the edge 9M, but this tightening is made and maintained by a winding band 45. Band 45 winds completely around the closing device, engaging itself, on one side, with the top part of the cap 3, and on the other side, with the external continuous circular edge 46 of the end 9M of the test tube. Band 45 can be a thermo-shrinking plastic material, and, while the undercap 4M is kept compressed to the edge 9M, the band is submitted to, for example, hot air, and caused to axially shrink, locking the closing device onto the test tube in a hermetic condition. If the material of the band 45 is metallic or of any other suitable material, the sole variation would be the different techniques used for fastening the band.

The central and external portions 4M and 5M of the undercap 2 and the similar portions 6M and 7M of the cap 3 are joined together by a co-molding or overmolding process. The coupling between the cap and undercap is provided by a thread as in the case of FIG. 1, but it is obvious that both the connection of the portions and the coupling between the cap and undercap could be made as shown in FIGS. 6 to 12.

A closing system having a lever which acts directly on the cap and indirectly on the interposed undercap can be used. This system, known as an irreversible toggle, is widely known and used for containers of gaseous liquids or for hermetic sealing mainly for the storage of liquids and/or solids foodstuffs.

Figure 21:
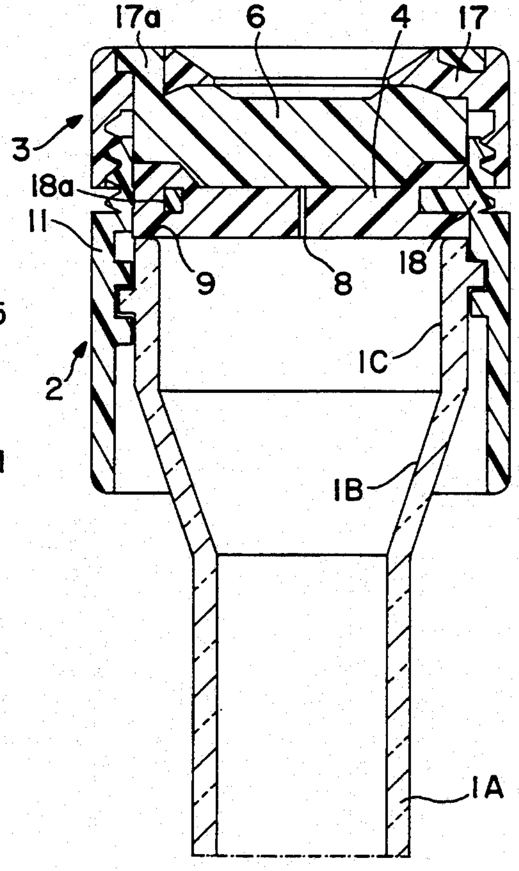
FIG. 21 is a cross-sectional view of the closing device of FIG. 1, mounted on a container having a tapered opening.

FIG. 21 illustrates the closing device mounted on a container with a tapered opening. In particular, the container is formed by a lower cylindrical part 1A, by an intermediate frusto-conical part 1B and a superior part 1C, also cylindrical in shape, but having a diameter larger than the diameter of the lower part. The shape of the container is particularly suitable for test tubes used for holding blood of which the erythrosedimentation rate (E.S.R.) is to be measured.

The closing devices shown in FIGS. 1 to 5 and 7 to 21 have the cap and the undercap locked directly on the undercap and on the container, respectively. Further, the bottom of the undercap is prearranged for the introduction of a drilled rod-type element into the container, and includes the machining of a through incision 8 formed by flexible edges normally fitted together to form a liquid seal.

Figure 22:
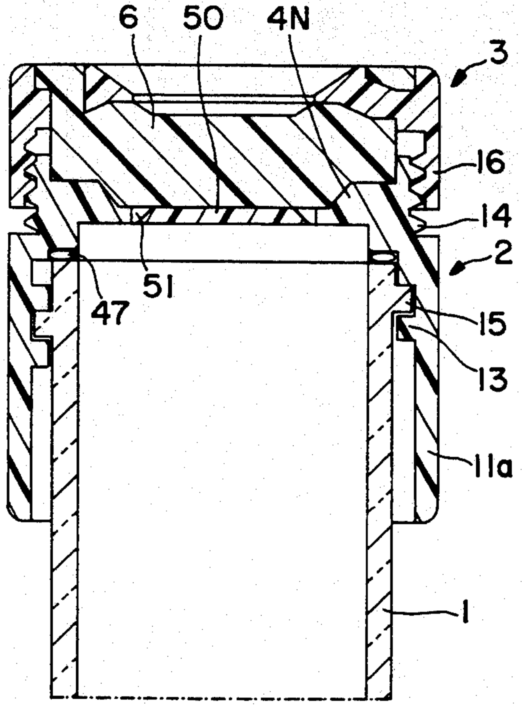
FIG. 22 is a cross-sectional view of another embodiment of the safety closing device and container of the invention.
Figure 23:
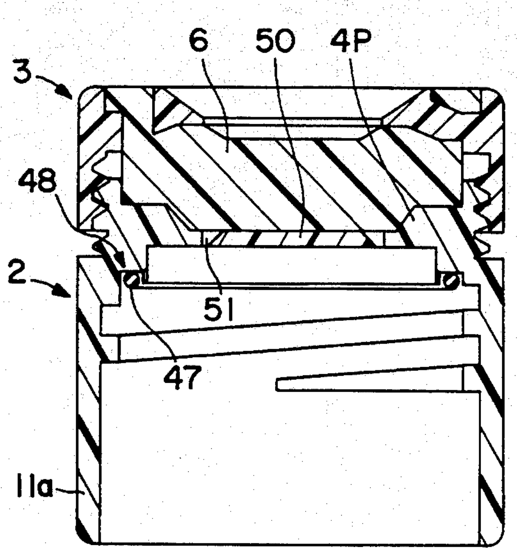
FIG. 23 is a cross-sectional view of the closing device of FIG. 22.

FIGS. 22–27, show the undercap locked on the edge of the container with a sealing annular element disposed therebetween. Further, the above mentioned prearrangement on the bottom of the undercap is comprised of a zone with a preestablished fracture as described in the following. In detail, FIG. 22 shows the annular sealing element formed by an elastic ring (O-ring) 47. FIG. 23 shows the annular element which is inserted in an annular groove 48 of the undercap 4P before the assembly of the closing device onto the container.

Figure 24:
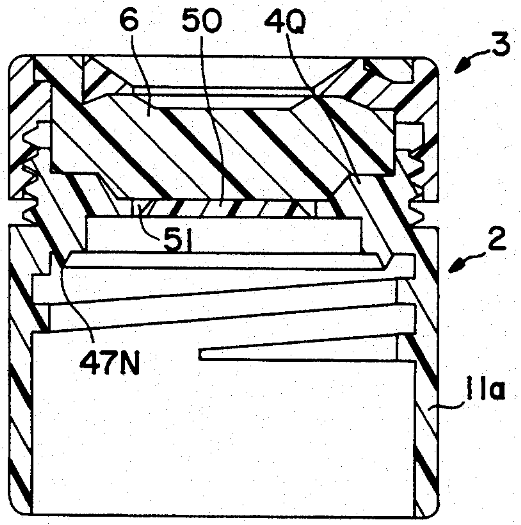
FIG. 24 and 25 illustrate two embodiments of the annular sealing element of the closing device of FIG. 22.
Figure 25:
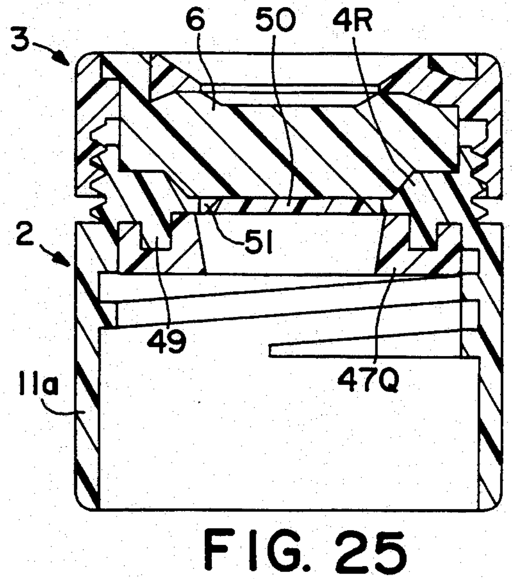

The device of FIG. 24 has the annular sealing element formed by a lower edge 47N of the undercap, having a triangular cross-section, while the device of FIG. 25 includes an annular sealing comprised of a ring 47Q co-molded or overmolded or assembled onto the internal edge 49 of the undercap 4R. The use of an annular sealing element is particularly advantageous when using an undercap formed by a single piece as shown in FIG. 12. In this case, the material of the undercap should be selected to have only characteristics suitable for assuring the mechanical anchoring of the undercap to the cap and to the container, leaving the elastic annular element to provide the sealing function. Naturally, an elastic annular element could also be used for the sealing between the cap and undercap.

FIGS. 22 to 25 show the bottom of the undercap including a perforable breakable central part 50 having a reduced thickness and provided with a circular tearing or preincision line 51, for establishing a preestablished fracture. In operation, after having removed the cap 3, a drilled rod-type element, such as a pipette or a pipette tip is pressed against the central part 50 to cause its partial or total separation from the bottom of the undercap 2 and the rod-type element can be further introduced into the inside of the container for blood drawing, etc.

The zone with the preestablished fracture can be also made by tearing or preincision lines converging towards the center of part 50, i.e., located radially, so that the opening of the bottom is established by detaching or straddling the flexible engraved elements which close tightly after the pipette or tip is removed from the container.

Figure 26:
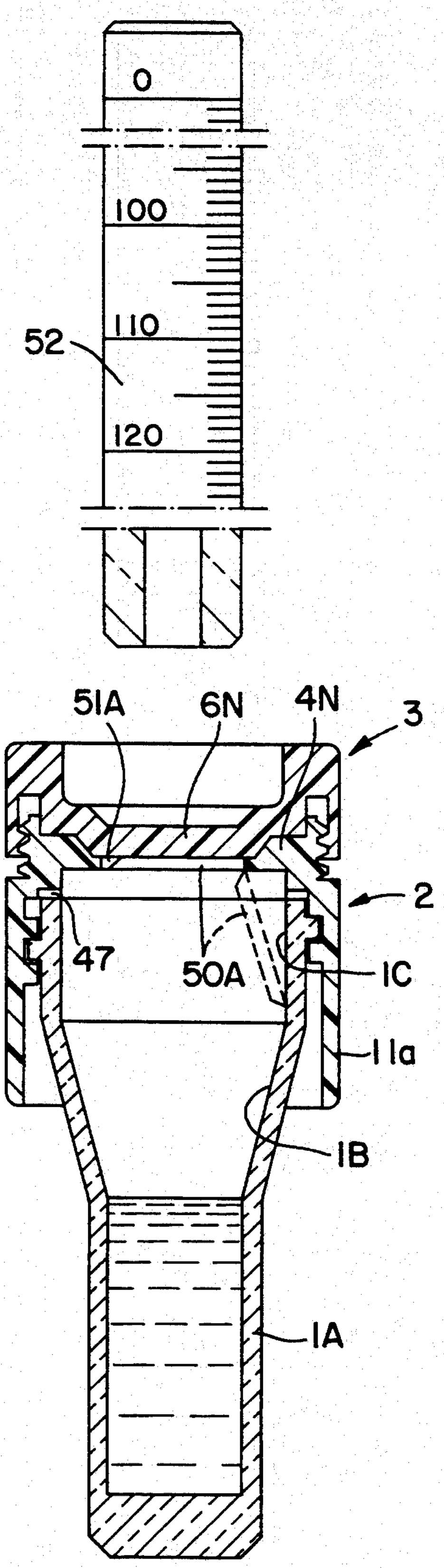
FIG. 26 shows the device of FIG. 22 mounted on a container with a tapered opening, wherein the cap is formed by a single piece and a graduated pipette is located over the test tube holding blood for the measurement of the blood erythrosedimentation rate (E.S.R.).
Figure 27:
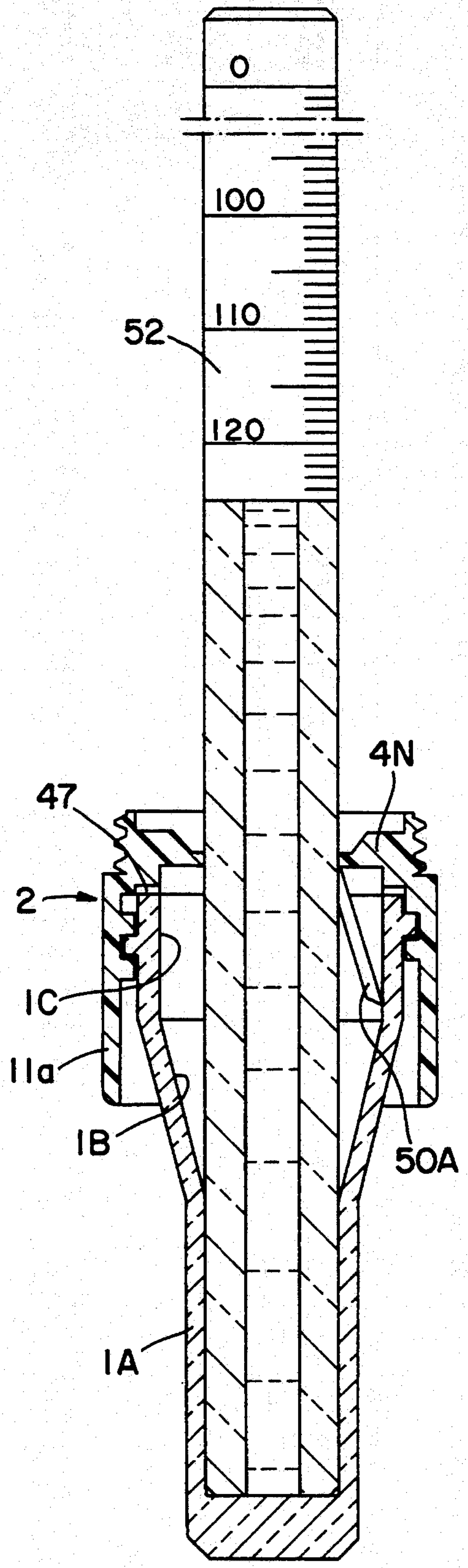
FIG. 27 shows the device of FIG. 26 with the graduated pipette inserted into the container after the removal of the cap.

FIGS. 26 and 27 show another embodiment of the central part with a preestablished fracture of the undercap. This central part identified by reference numeral 50A is produced by a tearing or preincision line 51A approximately circular in shape and extending slightly less than 360 degrees on the bottom of the undercap so that, after having pressed the drilled rod-type element against the part 50A, this part is removed from the bottom providing the opening, but remains connected to the bottom by a non-engraved appendix.

In particular, FIG. 26 shows the closing device mounted on a test tube filled with blood of which the erythrosedimentation rate (E.S.R.) is to be measured using a graduated pipette 52 shown above the test tube prior to measurement.

FIG. 27 shows the graduated pipette inserted into the test tube, after having removed the cap, and the central breakable perforable pre-engraved part 50A is partially detached from the bottom of the undercap 4N. The execution of the erythrosedimentation rate (E.S.R.) is known and, for a detailed description, reference is made to European Patent No. 0 108 724.

Satisfactory results are obtained with the use of plastic materials for both the cap and undercap, but it is clear that portions of these components, particularly the external parts, can be made of different materials such as aluminum, various metals, thermoplastic or thermosetting resins, various fibers, etc.

Finally, it should be noted that the different embodiments of the closing device according to the present invention, form a closed circuit system by which operations involving blood (filling of test tube, access to its inside, blood drawing, etc.) occur in such a way as to completely avoid the operator coming in contact with the liquid.

Although the present invention has been described in relation to particular embodiments thereof, many other variations and modifications and other uses will become apparent to those skilled in the art. It is preferred, therefore, that the present invention be limited not by the specific disclosure herein, but mainly by the appended claims.

What is claimed is:

1. A safety closing device for containers of biological liquids, particularly test tubes holding blood introduced therein, comprising:

an undercap removably locked on an open end of a container, the undercap including at least a central portion of elastic pierceable material, with a facing surface the central portion including central openable means for allowing the insertion into the container of means for introducing and drawing biological liquid to and from the container, the central portion being sealingly engaged with an edge of the open end of the container for guaranteeing a pneumatic and liquid seal along the edge;

a cap rotationally, removably locked on the undercap, the cap including at least a central portion of elastic pierceable material to allow insertion of the introducing and drawing means having a facing surface, a peripheral surface of the central portion of the cap being sealingly engaged with a corresponding facing peripheral surface of the central portion of the undercap to guarantee a pneumatic and liquid sealing of the container, the facing surfaces of the central portions of the undercap and cap being closely engaged with one another to eliminate any free space therebetween, wherein the insertion of the introducing and drawing means through the central openable means of the undercap occurs after the removal of the cap from the undercap; and locking means disposed on at least one of the cap and undercap for mechanically and axially coupling the cap and undercap on the open end of the container, wherein said locking means is removable only by intentional disengagement.

2. A safety closing device for containers of biological liquids, comprising:

an undercap removably locked on an open end of a container;

means located in the undercap for allowing insertion of means for filling and drawing biological liquid to and from the container, the means for allowing insertion comprising a central portion of perforable material, the central portion being sealingly engaged with an edge of the open end of the container and having a facing surface;

a cap rotationally, removably locked on the undercap for sealing the undercap, the cap including at least a central portion of perforable material sealingly engaged with the central portion of the undercap having a facing surface, the facing surfaces of the central portions of the undercap and cap being closely engaged with one another to eliminate any free space therebetween; and locking means disposed on at least one of the cap and undercap for mechanically and axially coupling the cap and undercap on the open end of the container, wherein said locking means is removable only by intentional disengagement.

3. A safety closing device for containers of biological liquids, comprising:

an undercap removably locked on an open end of a container, the undercap including at least a central portion of elastic perforable material for allowing insertion of means for filling and drawing biological liquid to and from the container, the central portion including an incision having flexible edges normally closed to form a liquid seal which allows the insertion of the introducing and drawing means, the central portion being sealingly engaged with an edge of the open end of the container;

a cap rotationally, removably locked on the undercap for sealing the undercap, the cap including at least a central portion of elastic perforable material which allows insertion of the introducing and drawing means, the central portion of the cap having an annular surface sealingly engaged with a corresponding annular surface of the central portion of the undercap by an axial pressure, wherein the elastic central portions of the cap and undercap assure a liquid and pneumatic seal between the cap and undercap, and the undercap and the edge of the container, respectively; and locking means disposed on at least one of the cap and undercap for mechanically and axially coupling the cap and undercap on the open end of the container and for providing the axial pressure for sealing the central portions of the cap and undercap, wherein said locking means is removable only by intentional disengagement.

4. The safety closing device of claim 3, wherein the central portion of the cap has a convex shape and the central portion of the undercap has a concave shape, the convex shape of the central portion of the cap closely engaging the concave shape of the central portion of the undercap to eliminate any spaces therebetween.

5. The safety closing device of claim 3, further comprising a sheet of impermeable perforable material extending across the open end of the container, the central portion of the undercap communicating with the sheet.

6. The safety closing device of claim 3, wherein said increase in the central portion of the undercap includes a central zone with a pre-established fracture for the introduction of means for drawing blood from or for introducing blood into the container for purposes of analysis or data survey of the blood in the container.

7. The safety closing device of claim 6, wherein the preestablished fracture comprises a reduced thickness which can be perforated by the means for drawing blood.

8. The safety closing device of claim 6, wherein the preestablished fracture comprises a preincision line which can be perforated by the means for drawing blood.

9. The safety closing device of claim 6, wherein the preestablished fracture comprises a circular tearing line which extends almost 360 degrees on the bottom of the central portion of the undercap for allowing the introduction of a graduated pipette into the container for measuring blood erythrosedimentation rate.

10. The safety closing device of claim 3, further comprising an annular sealing element disposed between the central portion of the undercap and the edge of the container.

11. The safety closing device of claim 10, wherein the central portion of the undercap includes a seat and the annular element is located within the seat.

12. The safety closing device of claim 10, wherein the annular element comprises a ring co-molded with an internal edge of the central portion of the undercap.

13. The safety closing device of claim 10, wherein the annular sealing element comprises a ring over-molded onto an internal edge of the central portion of the undercap.

14. The safety closing device of claim 10, wherein the annular element is a ring of elastic material.

15. The safety closing device of claim 14, wherein the annular sealing element comprises an axial edge having a triangular cross-section disposed on the central portion of the undercap.

16. The safety closing device of claim 3, wherein the undercap and the cap each include a whole external portion closely connected to the respective central portion.

17. The safety closing device of claim 16, wherein the external portion of the undercap extends upwardly to engage the external portion of the cap.

18. The safety closing device of claim 16, wherein the external portion of the undercap extends axially around and downward a suitable length on the container to prevent contact with a bottom internal surface of the central portion of the undercap when the undercap is removed from the container.

19. The safety closing device of claim 16, wherein the external portion of the cap extends axially around and downward a suitable length on the container to prevent contact with a bottom internal surface of the central portion of the undercap when the undercap is removed from the container.

20. The safety closing device of claim 16, wherein the container includes an external wall and the external portion of the cap extends downward to engage the external wall of the container.

21. The safety closing device of claim 16, wherein the cap is a single piece formed by a sheet of impermeable perforable material and the external portion of the undercap includes a facing edge, said sheet being fixed to the facing edge of the external portion of the undercap.

22. The safety closing device of claim 16, wherein the locking means for mechanically coupling the cap and undercap comprises a thread disposed on the external portion of the undercap which engages a thread on the external portion of the cap, each of the threads having a single or a plurality of starts.

23. The safety closing device of claim 16, wherein the locking means comprises an external edge disposed on the container which engages with an internal edge on the external portion of the undercap to hold the undercap on the container.

24. The safety closing device of claim 16, wherein the locking means comprises a ring having a triangular cross-section disposed on the external portion of the undercap fused to the edge of the container.

25. The safety closing device of claim 16, wherein the locking means comprises internal radial projections disposed on the external portion of the undercap which engage corresponding radial external projections disposed on the container for securing the undercap to the container.

26. The safety closing device of claim 25, further comprising an anti-unscrewing device disposed between the external portion of the undercap and the container for preventing accidental disengagement.

27. The safety closing device of claim 16, wherein the central portion and external portion of the undercap are comprised of different materials, the central portion of the undercap being comprised of a material suitable for sealing the container and the external portion being comprised of a material having a strength suitable for coupling and uncoupling of the external portion of the cap and the external wall of the container.

28. The safety closing device of claim 27, wherein the central and the external portions of the undercap are made of moldable materials and the portions are connected together by a process of co-molding or over-molding.

29. The safety closing device of claim 28, wherein the material of the central portion of the undercap is a soft plastic and the material of the external portion of the undercap is a hard plastic.

30. The safety closing device of claim 29, wherein the central and external portions of the undercap include reciprocal co-penetrating parts for connecting the soft plastic material of the central portion to the hard plastic material of the external portion, wherein the co-penetrating parts form a perfect anchoring between the central and external portions of the undercap and provide liquid and pneumatic sealing between the undercap and the container.

31. The safety closing device of claim 16, wherein the container includes an external wall, and the external portion of the undercap extends downward to engage the external wall of the container.

32. The safety closing device of claim 31, wherein the locking means for mechanically coupling the undercap and container comprises a thread disposed on an inner part of the external portion of the undercap which engages a thread formed on the upper end of the external wall of the container.

33. The safety closing device of claim 32, wherein the threads between the external portions of the cap and undercap and the threads between the inner part of the external portion of the undercap and the container have opposite winding directions.

34. The safety closing device of claim 32, wherein the threads between the inner part of the undercap and the container have windings in the counterclockwise direction.

35. The safety closing device of claim 16, wherein the central portion and external portion of the cap are comprised of different materials, the central portion of the cap being comprised of a material suitable for sealing the undercap and the external portion being comprised of a material having a strength suitable for coupling and uncoupling of the central portion of the undercap and the external wall of the container.

36. The safety closing device of claim 35, wherein the central and the external portions of the cap are made of moldable materials and the portions are connected together by a process of co-molding or over-molding.

37. The safety closing device of claim 35, wherein the central portion of the undercap is comprised of at least two separate parts formed by molding or shearing, said at least two separate parts being adhered to each other and sealingly assembled with the external portion of the undercap before or during the placement of the closing device on the container.

38. The safety closing device of claim 35, wherein the central portion of the cap is comprised of at least two separate parts formed by molding or shearing, said at least two separate parts being adhered to each other and sealingly assembled with the external portion of the cap before or during the placement of the closing device on the container.

39. The safety closing device of claim 35, wherein the material of the central portion of the cap is a soft plastic and the material of the external portion of the cap is a hard plastic.

40. The safety closing device of claim 39, wherein the central and external portions of the cap include reciprocal co-penetrating parts for connecting the soft plastic material of the central portion to the hard plastic material of the external portion where the co-penetrating parts form a perfect anchoring between the central and external portions of the cap and provide liquid and pneumatic sealing between the undercap and the container.

41. The safety closing device of claim 16, wherein the locking means comprises a tightening band disposed around the external portions of the undercap and cap and the edge of the container to axially lock the undercap and cap to the container.

42. The safety closing device of claim 41, wherein the tightening band is made of a thermo-shrinking material.

43. The safety closing device of claim 41, wherein the tightening band is made of metal.

44. The safety closing device of claim 41, wherein the locking means further comprises a thread disposed on the external portion of the undercap which engages a thread on the external portion of the cap.

* * * * *